(12) United States Patent
Gillies et al.

(10) Patent No.: US 8,406,837 B2
(45) Date of Patent: Mar. 26, 2013

(54) MEANS AND METHODS FOR CYTOMETRIC THERAPIES

(75) Inventors: George T. Gillies, Charlottesville, VA (US); Helen Fillmore, Richmond, VA (US); William C. Broaddus, Midlothian, VA (US); Boyd M. Evans, III, Oak Ridge, TN (US); Stephen W. Allison, Knoxville, TN (US)

(73) Assignees: UT-Battelle, LLC, Oak Ridge, TN (US); University of Virginia Patent Foundation, Charlottesville, VA (US)

( * ) Notice: Subject to any disclaimer, the term of this patent is extended or adjusted under 35 U.S.C. 154(b) by 679 days.

(21) Appl. No.: 12/513,258

(22) PCT Filed: Nov. 1, 2007

(86) PCT No.: PCT/US2007/023047
§ 371 (c)(1),
(2), (4) Date: Mar. 17, 2010

(87) PCT Pub. No.: WO2008/057370
PCT Pub. Date: May 15, 2008

(65) Prior Publication Data
US 2010/0210927 A1 Aug. 19, 2010

Related U.S. Application Data

(60) Provisional application No. 60/855,956, filed on Nov. 1, 2006, provisional application No. 60/873,314, filed on Dec. 7, 2006.

(51) Int. Cl.
*A61B 5/00* (2006.01)
(52) U.S. Cl. .................................................... 600/321
(58) Field of Classification Search .................. 600/317, 600/321
See application file for complete search history.

(56) References Cited

U.S. PATENT DOCUMENTS

| | | | |
|---|---|---|---|
| 2003/0064025 A1* | 4/2003 | Yang et al. | 424/9.6 |
| 2003/0204171 A1* | 10/2003 | Kucharczyk et al. | 604/264 |
| 2008/0013960 A1* | 1/2008 | Tearney et al. | 398/139 |

FOREIGN PATENT DOCUMENTS

WO    WO 02/38040 A2    5/2002

OTHER PUBLICATIONS

Doudet D. J. et al., "PET imaging of implanted human retinal pigment epithelial cells in the MPTP-induced primate model of Parkinson's disease", *Experimental Neurology* 189: 361-368 (2004).

(Continued)

*Primary Examiner* — Clayton E Laballe
*Assistant Examiner* — Noam Reisner
(74) *Attorney, Agent, or Firm* — Scully, Scott, Murphy & Presser, P.C.

(57) ABSTRACT

A functionalized tip is incorporated into catheters for the cytometric delivery of cells into the brain and other body parts. For use in the brain, the tip forms part of a neurosurgical probe having a proximal end and a distal end. In addition to the functionalized tip, the probe has at least one cell slurry delivery lumen and a plurality of optical fibers configured along the probe, terminating in the tip to provide the photo-optical capability needed to monitor the viability and physiological behavior of the grafted cells as well as certain characteristics of the cellular environment. Details are also presented of the use of a neurocatheter having a cytometric tip of the type disclosed in the invention, as employed within the context of a feedback and control system for regulating the number of cells delivered to the brain of a patient.

21 Claims, 20 Drawing Sheets

OTHER PUBLICATIONS

Anonymous, "Specialty Micro Components—45° Rod Lenses", Jul. 15, 2004 URL:http://www.edmundoptics.com/onlinecatalog/DisplayProduct.cfm?product=1413 (retrieved Mar. 25, 2011).

Communication dated Apr. 26, 2011, including a Supplementary Partial European Search Report in connection with European Patent Application No. 07839885.6.

* cited by examiner

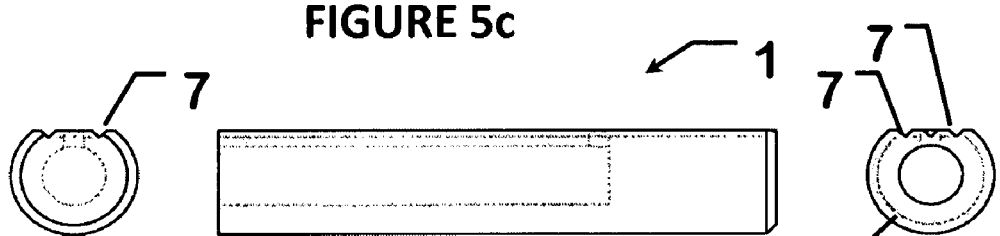
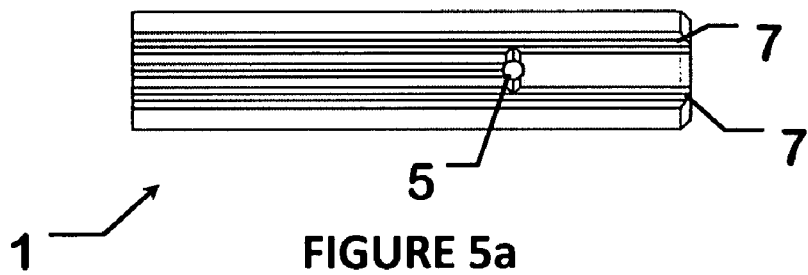

MEANS AND METHODS FOR CYTOMETRIC THERAPIES

CROSS-REFERENCE TO RELATED APPLICATIONS

This application claims priority from U.S. Provisional Patent Applications 60/855,956 and 60/873,314 filed on Nov. 1, 2006 and Dec. 7, 2006, respectively, both applications are herein incorporated by reference in their entirety.

STATEMENT REGARDING FEDERALLY SPONSORED RESEARCH

This invention was made with United States Government support under Contract No. DE-AC05-00OR22725 between the United States Department of Energy and U.T. Battelle, LLC. The United States Government has certain rights in this invention.

BACKGROUND OF THE INVENTION

Parkinson's disease (PD) is a devastating malady for which there is presently no cure. Moreover, there is also no means of arresting the progressive neurodegeneration experienced by most of those who suffer from it. Approximately 1.5 million Americans are afflicted by PD. Age appears to be a critical parameter in those that develop PD with those who are 50 and above being the largest group affected. Because this is a progressive disease with no known cure, interest remains high in refining treatment options involving cell transplantation as a possible therapy aimed at restoration and regeneration of the damaged dopaminergic circuitry in the brain. Crucial issues that must be confronted in the field of neural stem/progenitor cell transplantation (NPCs) include those pertaining to the delivery and survival of the cells in question. For cell replacement therapies to become a viable option for treatment of Parkinson's disease, several obstacles that derive from these issues must be overcome. For instance, it has been estimated that only 5-10% of cells transplanted into the central nervous system (CNS) survive post-transplantation, leaving only a small portion of the cells originally grafted to contribute in functional restoration. When considered at the most fundamental level, and as discussed further below, it is not even known with certainty that the cells that are delivered into the brain via the presently existing means and methods are alive either at the time of delivery or shortly thereafter, within the brain.

From a clinical perspective, the most pressing need in this field is one of improving cell survival following transplantation due to the low percentage of cells that survive in the host central nervous system. The vast majority of transplanted cells die within 24 hours of transplantation, and a significant fraction may be dead upon delivery, no matter their source or origin. Triggers that may initiate this neuronal death include: donor tissue hypoxia and hypoglycemia, mechanical trauma during the delivery process, free radicals, growth factor deprivation, and excessive extracellular concentrations of excitatory amino acids in the host brain tissues. Part of the underlying issue is that growth factor infusion has typically not been undertaken via the same catheter. More generally, the functional nature of the catheter, its placement in the brain, and the parameters of infusion all play critical roles in controlling the distribution of agents such as cell slurries. In addition, researchers have shown that increasing the amount of implanted tissue does not always increase the rates at which the cells survive and differentiate into dopamine-producing neurons in Parkinsonian models. Primate studies have shown that distributing small amounts of tissue over a larger area, i.e., in "micrografts" (as such procedures are called), results in significant areas of densely packed dopaminergic neurons. There is extensive outgrowth from these neurons as compared to subjects which were infused with a large amount of cell slurry in a very localized region (Sladek et al., 1998). These results and others have demonstrated that two important needs must be met: (1) it is imperative to deliver a highly-controlled amount of tissue (i.e., a fixed number of cells) into the host brain, and (2) a knowledge of cell viability at the delivery point is critical for moving in the direction of developing a clinically useful technique.

The prior art is largely silent on the issue of achieving satisfactory results for both of these needs simultaneously during the delivery process. For instance, Goldman et al. in U.S. Pat. No. 7,037,493 disclose a method and means for delivering a nucleic acid that codes for a neurotrophic factor, but their method and means does not allow the clinical user to perform in situ monitoring of the cells in order to make acute assessments of their viability upon delivery and chronic assessment of their functionality post-delivery. Similarly, Hammer et al. in U.S. Pat. No. 6,758,828 teach methods and means for cell storage and delivery but do not disclose techniques for monitoring cell number and viability during delivery. Gay et al. in their abstract "Development of a Combination Cell Delivery/Biosensor Catheter for the Monitoring of Dopamine from Differentiated Neuronal Cells," The Virginia Journal of Science, Vol. 55, p. 28, (2004), suggest a multi-probe means for introducing sensing instrumentation into a target location within the brain of a patient via a neurocatheter means, but that system is not designed for the cytometric monitoring and assessment of the cells during the delivery process.

A limitation of the prior art is that in general it discloses no methods or means for confirming cell viability during the delivery process. A second limitation of the prior art is that in general it discloses no methods or means for cytometrically counting the number of cells that traverse the catheter and enter the brain during the delivery process. Another limitation of the prior art is that it does not foresee photo-optical means to carry out the functions of viability confirmation and NPC cytometry in situ during the cell delivery process. Still another limitation of the prior art is that it does not foresee the incorporation of photo-optical means into neurocatheterization devices for the purpose of carrying out the in situ viability confirmation and NPC cytometry during the cell delivery process.

To lay the foundation for overcoming these limitations, means and methods for the incorporation of optical fibers into neurocatheters for use during the delivery of cells and other therapeutic agents into the brain were invented. This invention teaches methods and means for coupling the optical fibers into specialized distal tips of neurocatheters such that the optical fibers have full functionality in techniques for viability confirmation and NPC cytometry during the cell delivery process.

BRIEF DESCRIPTION OF THE INVENTION

The invention is in the field of medical implants. More specifically, the invention relates to the field of neurocatheters (broadly known as catheters), both acute and in-dwelling, that are placed surgically in a patient, such as the brain of a patient. Most specifically, the invention relates to that class of neurocatheter that can be used for the intraparenchymal delivery of diagnostic and therapeutic agents into targeted locations within the patient, such as the brain of the patient, and which can also be used simultaneously to make measurements of physiology (e.g., brain physiology) that are needed to optimize treatments aimed at alleviating the effects of diseases such as neurodegenerative diseases.

Means and methods for enabling the cytometrically monitored delivery of, for example, NPC's into CNS host tissues via a neurocatheter are taught. The neurocatheter might generally have a distal end and a proximal end and a plurality of axial lumens, as for instance in the devices disclosed by Kucharczyk et al. in U.S. Pat. Nos. 6,599,274 and 6,626,902, all incorporated by reference in their entirety herein. Regardless of its axial configuration, the neurocatheter has a distal tip that is configured so as to allow the placement of a plurality of optical fibers around at least one port hole on the distal tip. At least one port hole is used as the point of egress for the pumping of the cell slurry (e.g., NPC cell slurry) into the target location within, for example, the brain. The optical fibers are used to deliver light to and collect light from the region of the port hole, for the purpose of monitoring and counting the number of living cells being delivered through at least one port hole. Configurations of the optical fibers can also be used to measure and record the levels of the cell metabolites, including species such as dopamine, acetylcholine and the like, prior to, during and/or after the cell delivery process, as needed. Growth factors, nutrients, angiogenesis factors, and other agents needed to optimize the clinical outcome of the delivery and differentiation process can also be delivered through the neurocatheter, in order to maintain and nurture the neural niche microenvironment of the implanted cells. This will be done because numerous factors appear to influence implant viability in the CNS, including the stage of differentiation of the cells, the intraparenchymal site of placement of the cells and the techniques used in the preparation of the cells. Because of the specialized distal tip of the neurocatheter disclosed here, the neurocatheter will for the first time play a critical role in quantifying the distribution of, for example, NPCs in human brain. In addition, other currently used catheter-based techniques for intracerebral implantation of cells appear to provoke inflammatory tissue reactions, hemorrhage, necrosis, and degenerations. Such nonspecific traumatic changes at the implant site may compromise cell survival or even disrupt the architectural remodeling of vascular, glial and neuronal graft elements. These are all additional reasons for incorporating cytometric capabilities into the distal tip of the neurocatheter, in order to confirm cell count and minimize delivery time and tissue damage, while maximizing the chances for implant survival. Therefore, distal tip means and methods for its use with neurocatheters are the subject of the invention.

The invention is a catheter having a catheter body with an inner lumen, a distal end and a proximal end; a distal catheter tip body removably coupled to the catheter body distal end; at least one port hole in the catheter tip body; a plurality of alignment grooves axially aligned in the catheter tip body for the placement of optical fibers; a mating mechanism for coupling the tip body to the catheter body; at least one structural chamber for passing material from the inner lumen to at least one port hole; a plurality of optical fibers disposed in the alignment grooves to deliver light to and collect light proximate at least one port hole; a plurality of optical fiber stubs with at least one mirrored end for steering light to and from the optical fibers proximate at least one port hole. Further details of the invention and the methods and means for its practice are described in the accompanying drawings.

BRIEF DESCRIPTION OF THE DRAWINGS

FIG. 5 shows indications of the internal structure of the neurocatheter tip, as seen from above (FIG. 5A), from the proximal end (FIG. 5B), from the side (FIG. 5C), and from the distal end (FIG. 5D).

DETAILED DESCRIPTION OF THE INVENTION

When the neurocatheter is used in either acute or chronic delivery conditions, the readings from the optical fibers (which serve as a sensor or as sensors) within the distal tip can provide a variety of useful physiological data that can play a central role in the optimization of the therapeutic approach. For instance, recordings of dopamine level can provide a quantitative indication of the functionality of the cells, thus implying that they either have or have not reached a certain stage of maturity in the differentiation process. Those data would then form the basis for clinical-strategy decisions on the need for delivery of growth factors, the timing of the delivery of said factors, and cessation of delivery of said factors. This would be in addition to the primary use of the sensor or sensors as a means to assess cell viability, with the subsequent data then providing a basis for a clinical-strategy decision about the delivery of an angiogenesis factor for the purpose of increasing the microvascular blood supply at the delivery site, thus helping further oxygenate the cells and improve survival. Likewise, clinical-strategy decisions on all of the other critical aspects of the maintenance of the neural niche can also be made in the same manner, thus providing a quantitative basis for optimizing the clinical outcome of the procedure. These clinical-strategy decisions might be made within the context of an automated data processing system that operates on an algorithm used to realize a feedback loop that controls the overall cell delivery process. The feedback loop might be implemented in real time or with appropriate delays for data processing, biochemical reaction rates, and the like. In general, any neurocatheter or catheterization system incorporating the means and method of the invention might be used in conjunction with or in a means and method similar to the device and methods of use described by H. Fillmore and G. T. Gillies in U.S. Patent Application No. 60/846,011, "Cell Delivery means and Method with Optimization of the Neural Niche Microenvironment," filed Sep. 20, 2006, herein incorporated by reference.

Figure 1:
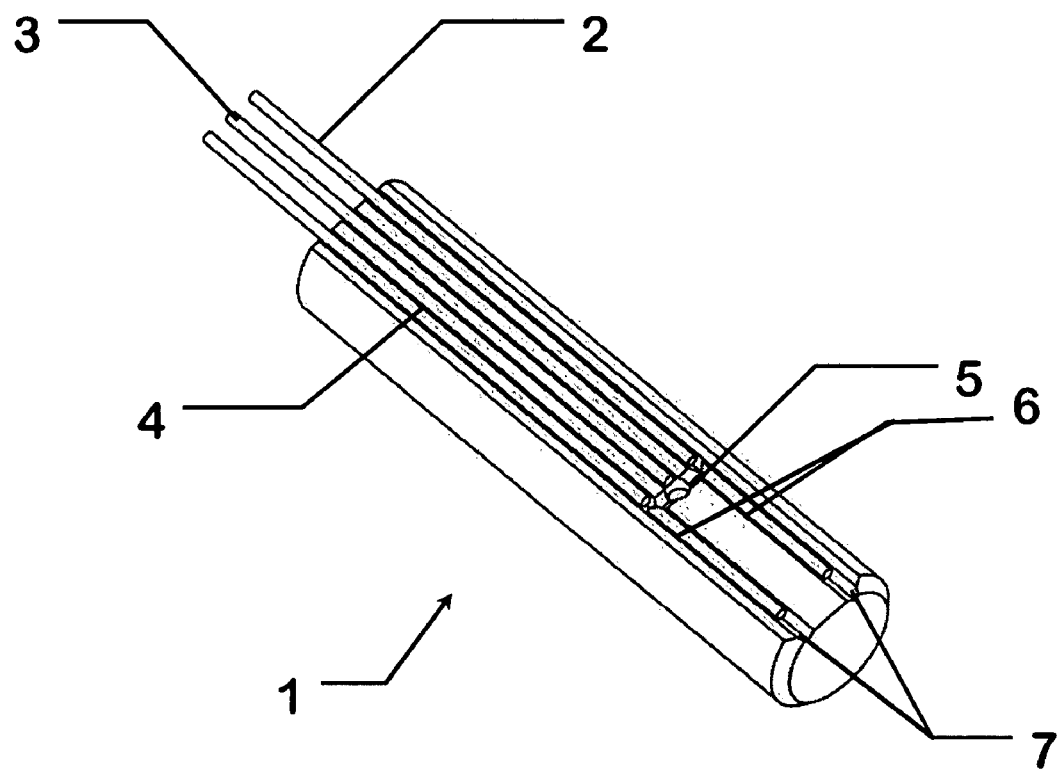
FIG. 1 shows an overview of the neurocatheter tip from the upper distal perspective.

FIG. 1 shows an embodiment of the invention. The body of the tip, 1, has a light delivery fiber, 2, a fluorescence and scatter measurement fiber, 3, and an attenuation measurement fiber 4. It also has two fiber stubs, 6, with 45° cuts at the proximal ends. The cut ends of stubs 6 are polished and metalized to form mirror surfaces. Fibers 2, 3, 4 and fiber stubs 6 are placed in fiber alignment grooves, 7, and configured around a side port hole, 5, as shown in the figure. Light from the delivery fiber 2 is reflected laterally across the port hole 5. As a slurry of fluorescent cells, such as autologous stem cells, is pumped through the port hole 5, photo-optical signals associated with the fluorescence and scattering of said cells are collected by fiber 3, and signals associated with the attention of the light by the cells are collected by fiber 4. The fibers convey the light along the neurocatheter, and eventually deliver it to a measurement means for analysis. Alternatively and/or additionally, said optical fibers and fiber stubs might be used as photo-optical sensors that monitor the levels of dopamine and other effluents in the interstitial space into which said cell slurry (e.g., autologous cell slurry) is being delivered.

Figure 2:
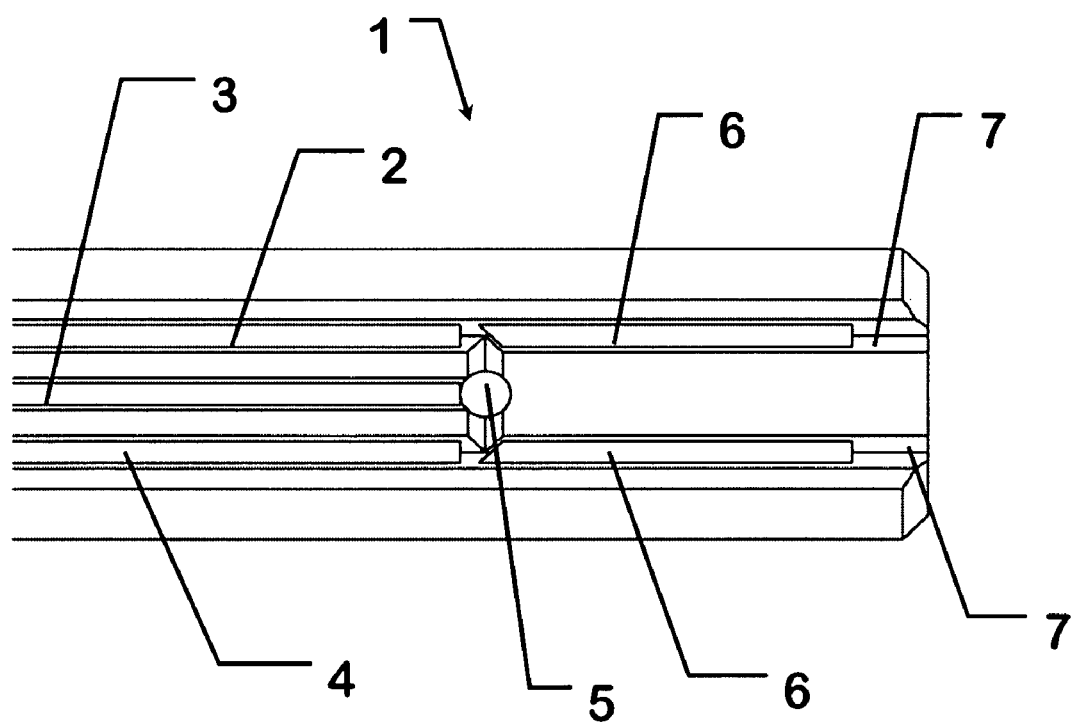
FIG. 2 shows a close-up view of the neurocatheter tip, as seen from directly above.

FIG. 2 shows all of the same elements as found in FIG. 1, but considered in a view from above.

Figure 3:
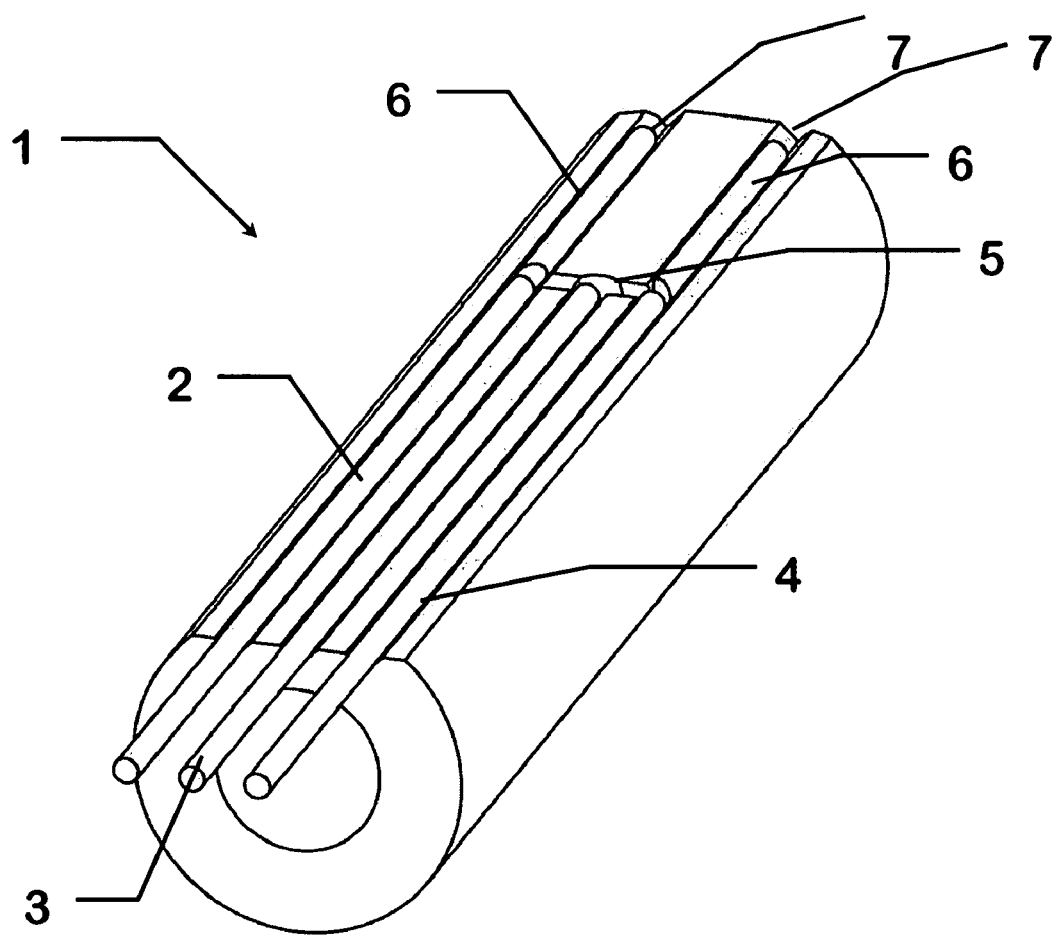
FIG. 3 shows an overview of the neurocatheter tip from the lower proximal perspective.

FIG. 3 shows all of the same elements as found in FIGS. 1 and 2, but considered from a lower proximal perspective.

Figures 4A, 4B:
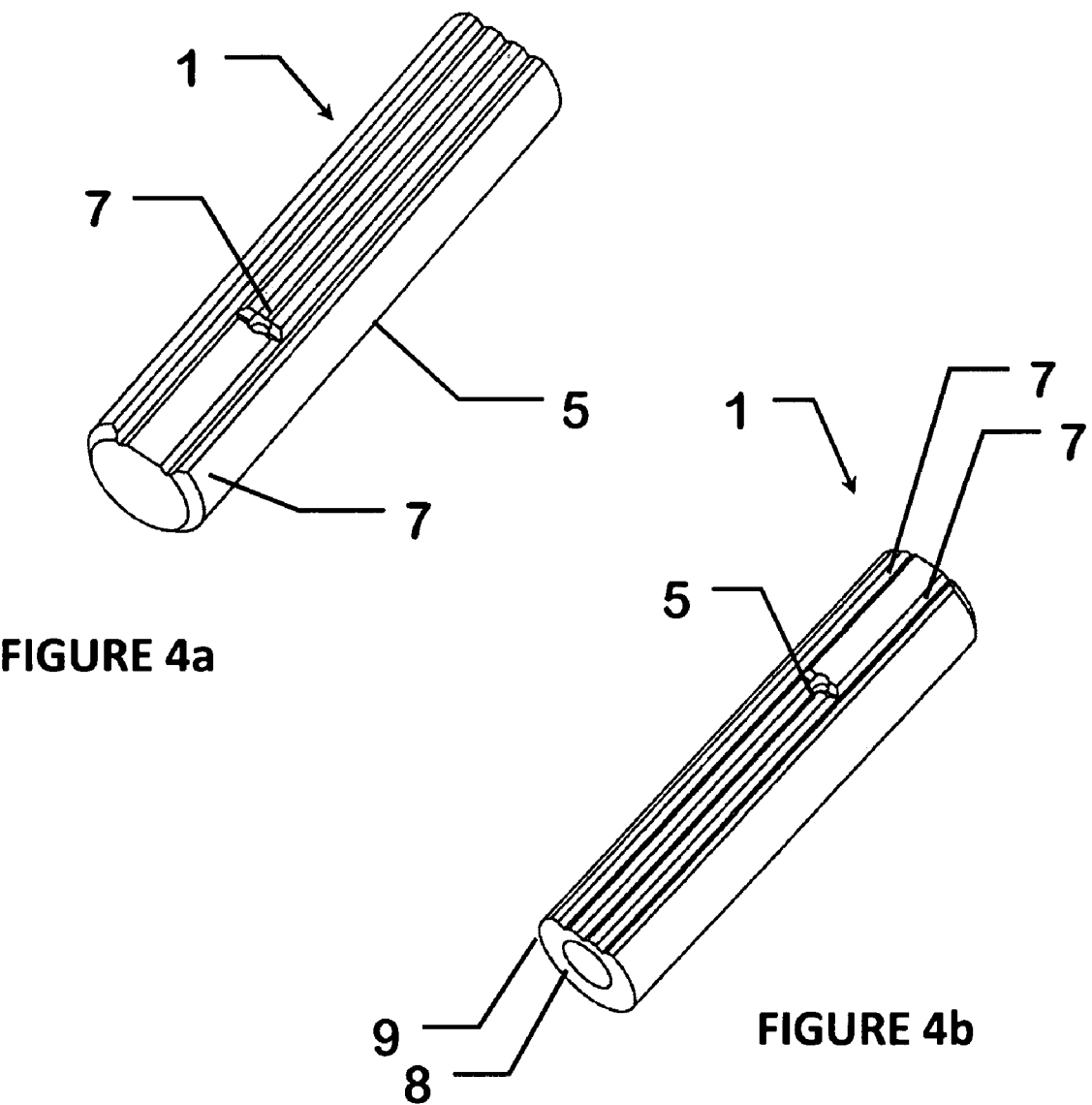
FIG. 4 shows indications of the internal structure of the neurocatheter tip, from the distal perspective (FIG. 4A) and from the proximal perspective (FIG. 4B).

FIG. 4 shows the internal structural chamber 8 in distal perspective in FIG. 4A and in proximal perspective in FIG. 4B. The coupling point, 9, of the tip and the neurocatheter is also shown in FIG. 4B. The internal structural chamber receives the flow of the cell slurry containing, for example, autologous stem cells, and conveys it to the port hole, 5. A mating mechanism connecting device such as a tubular mechanical sleeve or bushing is used to connect the tip body to a catheter body.

FIG. 5A shows the preferred embodiment as seen from above. FIG. 5B shows the preferred embodiment as seen from the proximal end. FIG. 5C shows the preferred embodiment as seen from the side. FIG. 5D shows the preferred embodiment as seen from the distal end.

Figure 6:
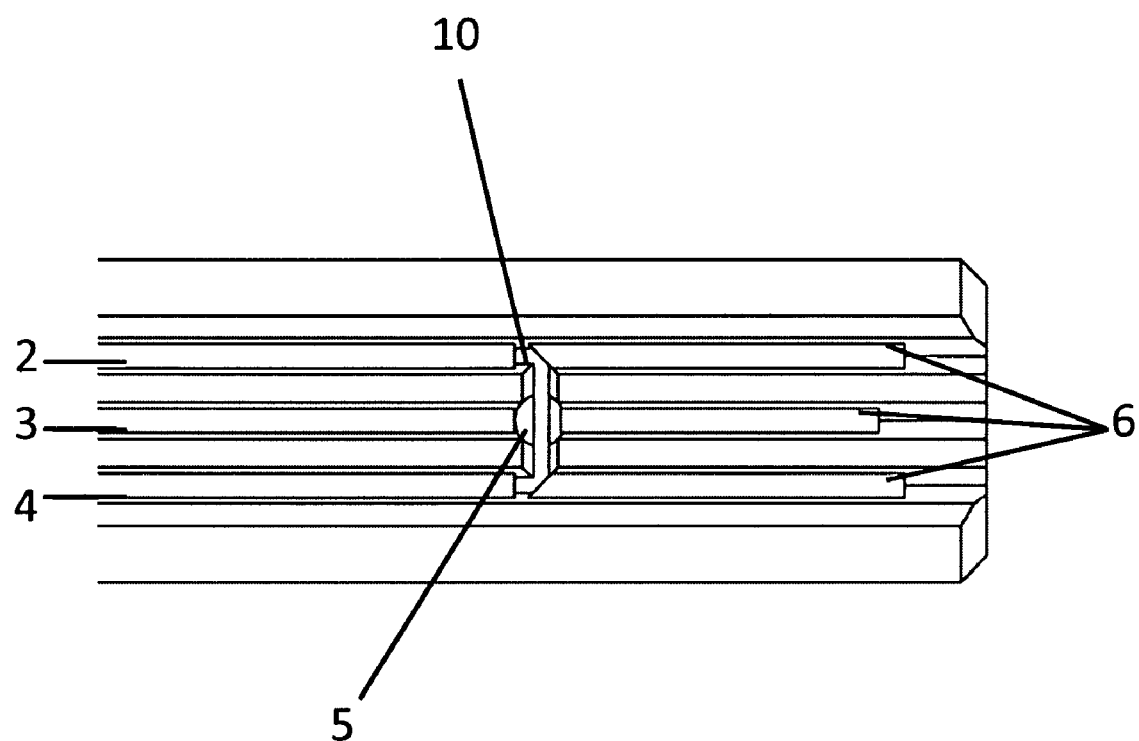
FIG. 6 shows an embodiment having three fiber stubs with the two outer stubs providing flat-faced reflection of the photo-optical signal.

FIG. 6 shows an embodiment having three fiber stubs 6 with flat-faced 45° cuts on the two outer stubs. The photo-optical signal 10 from delivery fiber 2 is reflected laterally across the port hole 5 maintaining essentially the same beam size. As a slurry of fluorescent cells (e.g., autologous stem cells) is pumped through the port hole 5, photo-optical signals associated with the fluorescence and scattering of said cells are collected by fiber 3, and signals associated with the attenuation of the light by the cells are collected by fiber 4. The fibers convey the light along the neurocatheter, and eventually deliver it to a measurement means for analysis. Alternatively and/or additionally, said optical fibers and fiber stubs might be used as photo-optical sensors that monitor the levels of dopamine and other effluents in the interstitial space into which said cell slurry, such as an autologous cell slurry or multiplural cell slurry, is being delivered.

Figure 7:
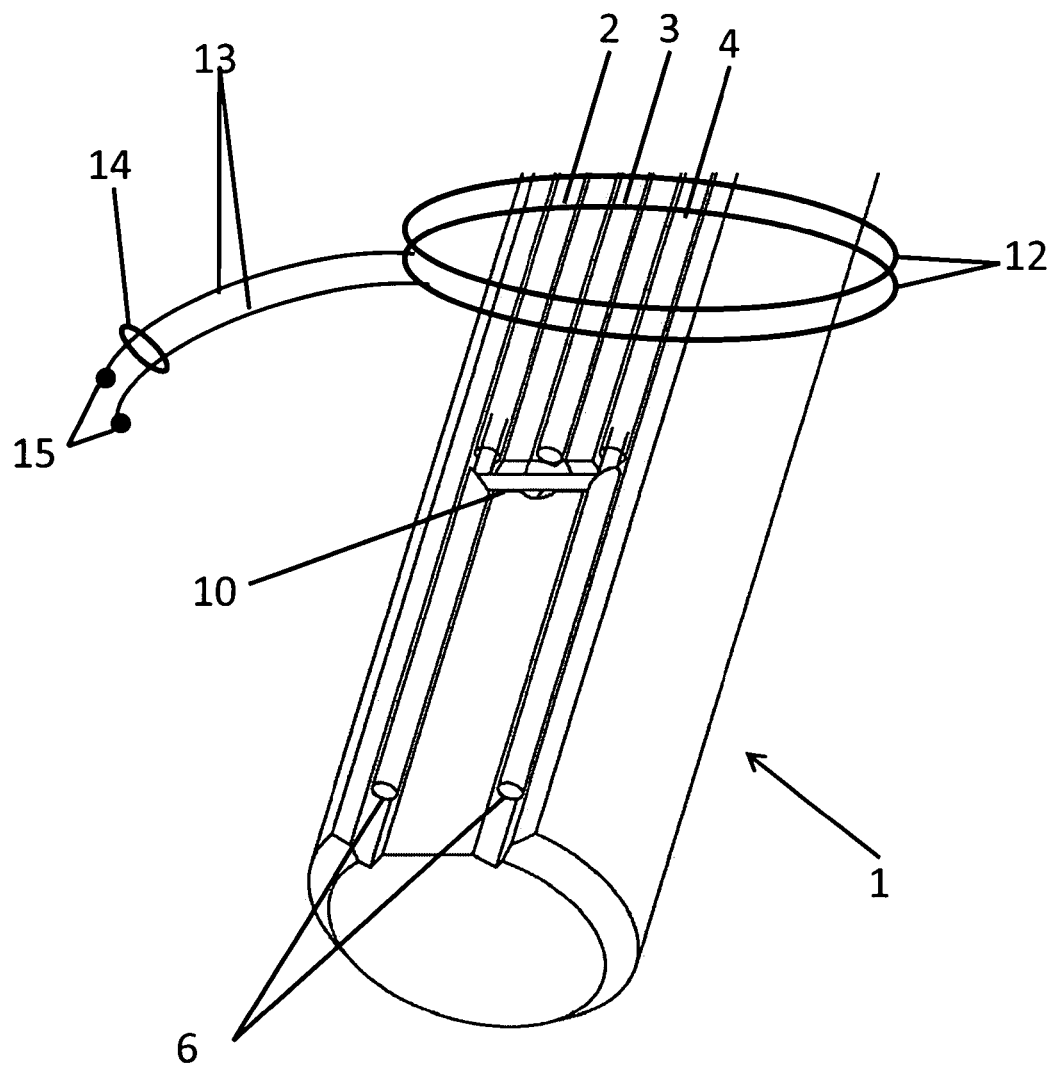
FIG. 7 illustrates an embodiment having two fiber stubs that provide flat-faced reflection of the photo-optical signal and micro-coils for MR contrast enhancement.

FIG. 7 illustrates an embodiment having two fiber stubs 6 that provide flat-faced reflection of the photo-optical signal and also micro-coils for MR contrast enhancement. Electrical micro-coils 12, with leads 13, shield 14, and connector points 15, are mounted on the body of neurocatheter tip 1. The micro-coils are used to increase the MR contrast of the tissues adjacent to the neurocatheter tip, thus improving the quality of the MR images. The photo-optical signal 10 from delivery fiber 2 is reflected laterally across the port hole 5 without altering the signal beam.

Figure 8:
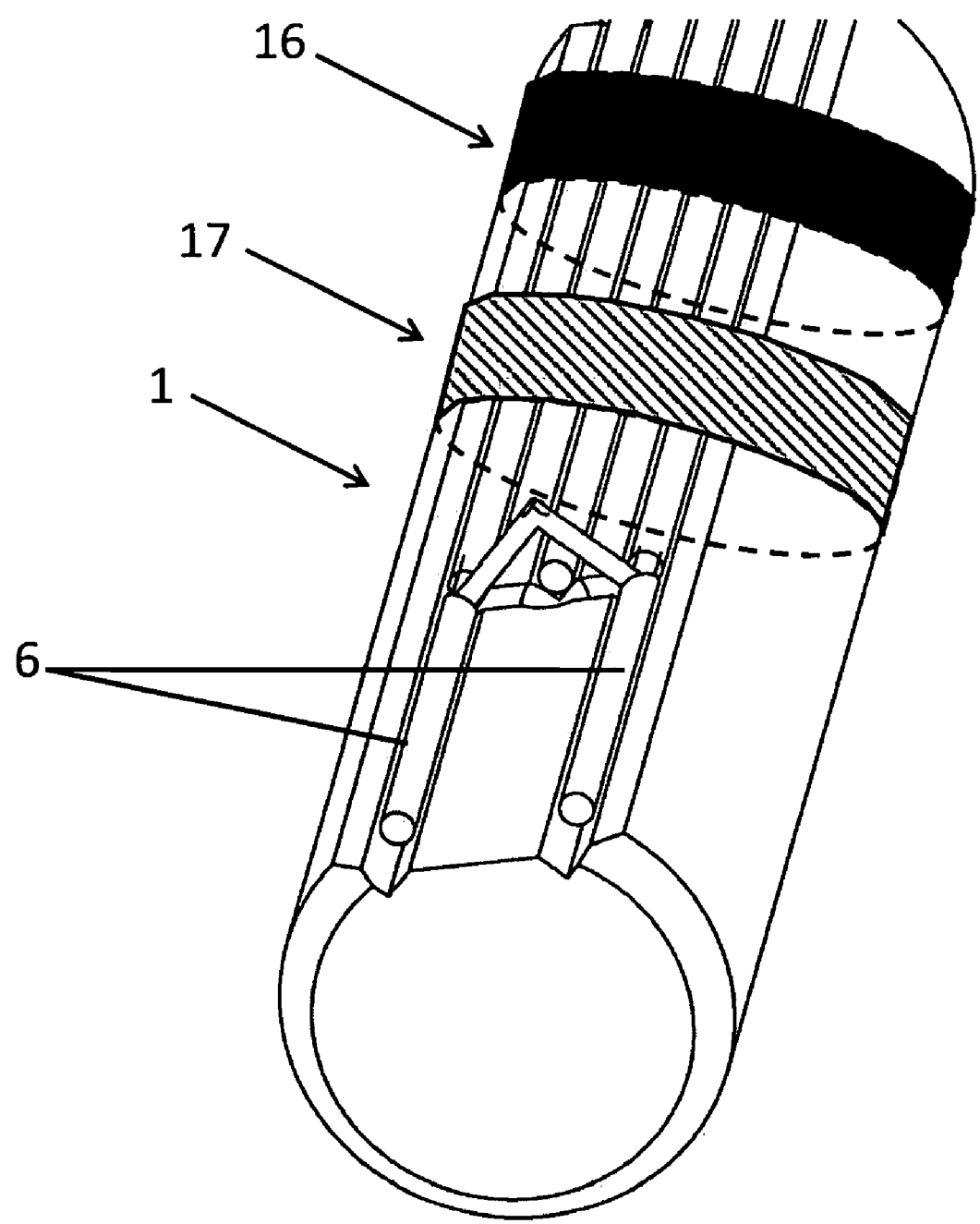
FIG. 8 shows the embodiment of FIG. 7 with the reflective fiber stubs rotated to focus the photo-optical signal in the interstitial space proximate the cell slurry exit point. Also, bands of material are shown to improve MR visibility and radio-opacity.

FIG. 8 shows the embodiment of FIG. 7 with the reflective fiber stubs 6 rotated to focus the photo-optical signal in the interstitial space proximate the cell slurry exit point. Also, bands of material are shown to improve MR visibility and radio-opacity. Bands of materials, 16 and 17, are used to improve the MR visibility and radio-opacity, respectively, of the neurocatheter tip. The presence of these bands of material thus helps to make the tip visible when used in various imaging modalities, including magnetic resonance imaging, computed tomography, fluoroscopy, and the like.

Figure 9:
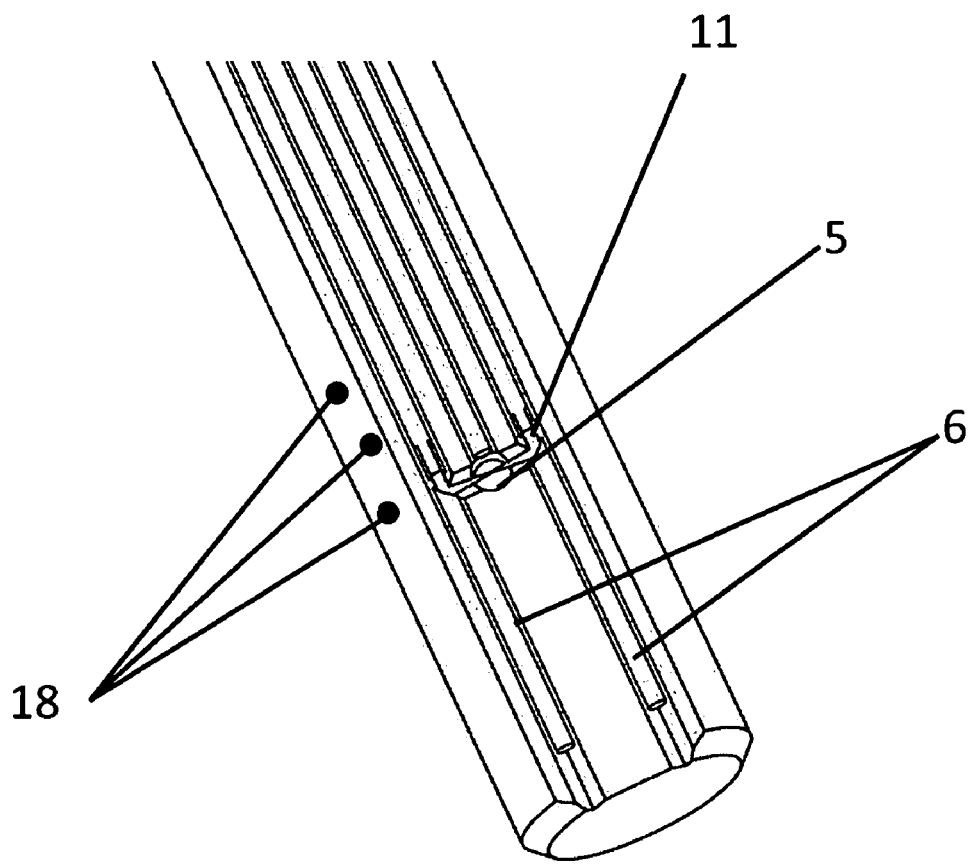
FIG. 9 shows an embodiment with two reflective fiber stubs having concave faces to narrow the focal point of the photo-optical signal and a plurality of port holes.

FIG. 9 shows an embodiment with two reflective fiber stubs 6 having concave faces to narrow the focal point of the photo-optical signal 11. The narrowed focal point provides for increased attenuation of the photo-optical signal as cells pass through the narrow focus of the beam. Also, a plurality of port holes 18 is shown in addition to the nominal port hole 5. Said port holes 18 might have similar fiber alignment grooves and fibers and fiber stubs associated with them, and/or they might be standard port holes with no such additional means configured about them. Said additional port holes 18 can be located anywhere convenient with regard to the structure of the neurocatheter tip, 1, including the front (end) of the distal tip.

Figure 10:
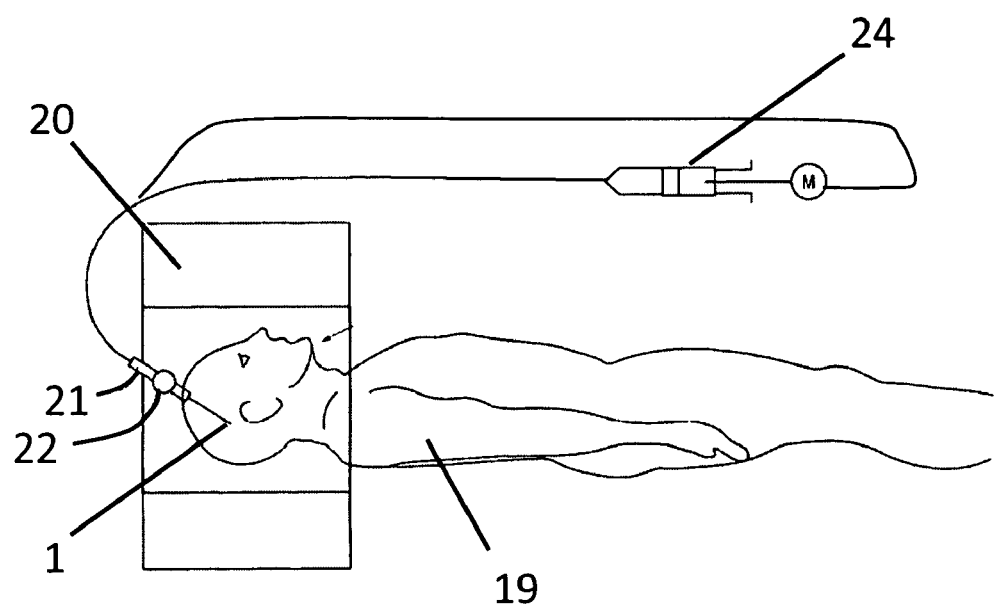
FIG. 10 shows a method of use of a neurocatheter having a subject tip.

FIG. 10 shows one preferred embodiment of a method of use of a neurocatheter having a tip of the type which is the subject of the invention. A patient, 19, is situated in an interventional surgical suite and an MR imaging means, 20. A neurocatheter, 21, and neurocatheter fixation device, 22, are being used to deliver a cell slurry, such as an autologous cell slurry, into the brain of the patient, 19. The neurocatheter tip, 1, which is the subject of the present invention, is positioned at the end of the neurocatheter means 21. The optical fibers, 26, that convey the photo-optical signals from the tip, 1, are connected to an optical transducer means, 27, which might be a plurality of photomultiplier tubes, photodiodes, charge-coupled devices (CCDs), or other photodetector system. The electrical signals from the transducer means, 27, are coupled into a measurement means, 28, which derives cytometric information about the numbers of cells (e.g., autologous stem cells) being delivered. The cytometric information from measurement means, 28, is used by an infusion control system, 29, to regulate the driving mechanism, 25, for the delivery syringe, 24, which then feeds the cell slurry (e.g., autologous cell slurry) through a delivery line, 23, to the neurocatheter means, 21. In this way, the clinicians carrying out the therapy can regulate the rates and amounts of cell slurry (e.g., autologous stem cell slurry) being delivered to the patient, 19. Similarly, this measurement and delivery means can also be used to monitor the amounts of dopamine and other effluents of the interstitital space during the therapy session or sessions, to make sure that the neural niche for the cells (e.g., autologous stem cells) has been prepared properly.

In another aspect, the present invention provides a method for in situ cytometric measurement of cell viability and count rates. The method comprises inserting the catheter described above into a patient. The patient can be any mammal. The mammal may be a farm animal, such as a goat, horse, pig, or cow; a pet animal, such as a dog or cat; a laboratory animal, such as a mouse, rat, or guinea pig; or a primate, such as a monkey, orangutan, ape, chimpanzee, or human. In a preferred embodiment, the mammal is a human.

The term "in situ" as used herein means that the cytometric measurement of cell viability and count rates occurs as the cells are being delivered by the catheter of the present invention to the patient.

The catheter can be inserted anywhere in the patient. Typically, the catheter is inserted in the organ or affected area that requires delivery of cells, such as NPCs. Examples of such areas include the brain, heart, liver, muscles, pancreas, etc.

The next step in the method for in situ cytometric measurement of cell viability and count rates includes delivering a cell slurry through a port hole of the catheter. The tern "cell slurry" as used herein refers to a suspension of cells. Typically, the cells are suspended in a media, which is typically a physiological acceptable buffered solution suitable for administration to a patient. Examples of such solutions include phosphate buffered saline and sodium chloride saline solution.

The concentration of the cell slurry is typically in the range of about $1 \times 10^4$ to about $1 \times 10^7$ cells per millimeter, and any intervening concentration, such as $5 \times 10^4$, $1 \times 10^5$, $2 \times 10^6$, etc. In a preferred embodiment, to optimize the signal strengths, the cells can be suspended in a high-density medium containing about $1 \times 10^6$ or more cells per millimeter during the delivery protocol. An additive can be added to increase the medium density and/or assists in keeping the cells more evenly suspended for a longer duration. Examples of additives include, but are not limited to, cellulose, ficoll-pague, sorbitol, manitol, sucrose, etc.

The cells are generally delivered at rates ranging from about 0.1 microliters per minute to about 100 microliters per minute, and any intervening rate, such as 0.3 microliters per minute, 0.5 microliters per minute, 1, microliters per minute, 10 microliters per minute, 70 microliters per minute, etc.

The cells in the cell slurry can be any cells useful for treating a disease or condition of a patient. Such cells typically depend on the condition being treated. One of skill in the art can readily determine the appropriate cell type to administer based on the disease or condition. For example, a patient suffering from Parkinson's Disease can be administered NPC. Similarly, a patient with liver disease can be administered, for example, liver cells. Likewise, a patient suffering from a cardiac disease can be administered, for example, cardiac muscle cells.

The cells in the slurry can be autofluorescent. As used herein, the term "autofluorescent" means that the cells exhibit autonomous fluorescence when excited with light at an appropriate wavelength. Alternatively, the cell can be transformed with a fluorescent vital stain. Methods for transforming a cell with a fluorescent vital stain are known to those skilled in the art. For example, the cell can be transfected with a nucleic acid sequence that encodes a fluorescent vital stain. An example of a vital fluorescent vital stain that can be used in the method of the present invention is green fluorescent protein (GFP). Other examples of fluorescent vital stains include rhodamine, FITC, etc. The autofluorescent and vital-stain methods can be used either separately or in unison via multi-photon arrangements.

The next step in the method for in situ cytometric measurement of cell viability and count rates includes exciting the cells with a wavelength of light to cause the cells to autofluorescence or cause fluorescence of the vital stain. The wavelength suitable for exciting the cells to autofluorescence or cause fluorescence of the vital stain can be readily determined by those skilled in the art for optimal signal reading. The excitation light sources for implementation of the method can include lasers, laser diodes, and light emitting diodes (LEDs). Once the photo-optical signals have been generated, optical fiber splitters may be employed to direct said signals to a plurality of detectors, either in support of independent measurements (eg., autofluorescent signals alone) or multi-photon measurements involving a plurality of signal generation modalities. Said optical fibers may be of either round or square cross-section, in the later case the square cross-section allowing for homogenization of the photo-optical signals within said fibers.

The next step in the method for in situ cytometric measurement of cell viability and count rates includes measuring autofluorescence or vital staining fluorescence of the cells. Any instrument suitable for measuring fluorescence can be utilized. The measurement of autofluorescence or vital staining fluorescence of the cell is a measurement of cell viability and count rates. For example, spectrometers can then be employed to analyze the signals and discern between scattered light, media fluorescence, and cell fluorescence, as might be done in one embodiment of the approach. One or more data analysis programs and one or more data processing systems (eg., a digital computer) can be used for implementation of the measurement and analysis process.

The subsequent data from the measurements can provide a basis for a clinical-strategy decision. For example, a growth factor can be also administered for the purpose of improving the viability of the delivered cell. Alternatively, for example, an angiogenesis factor can be administered for increasing the microvascular blood supply at the delivery site, thus helping further oxygenate the cells and improve survival. Likewise, clinical-strategy decisions on all of the other critical aspects of the maintenance of the neural niche can also be made in the same manner, thus providing a quantitative basis for optimizing the clinical outcome of the procedure. These clinical-strategy decisions might be made within the context of an automated data processing system that operates on an algorithm used to realize a feedback loop that controls the overall cell delivery process. Said feedback loop might be implemented in real time or with appropriate delays for data processing, biochemical reaction rates, and the like. In general, any neurocatheter or catheterization system incorporating the means and method of the invention might be used in conjunction with or in a means and method similar to the device and methods of use described by H. Fillmore and G. T. Gillies in U.S. Patent Application No. 60/846,011, "Cell Delivery means and Method with Optimization of the Neural Niche Microenvironment," filed Sep. 20, 2006.

Figure 11:
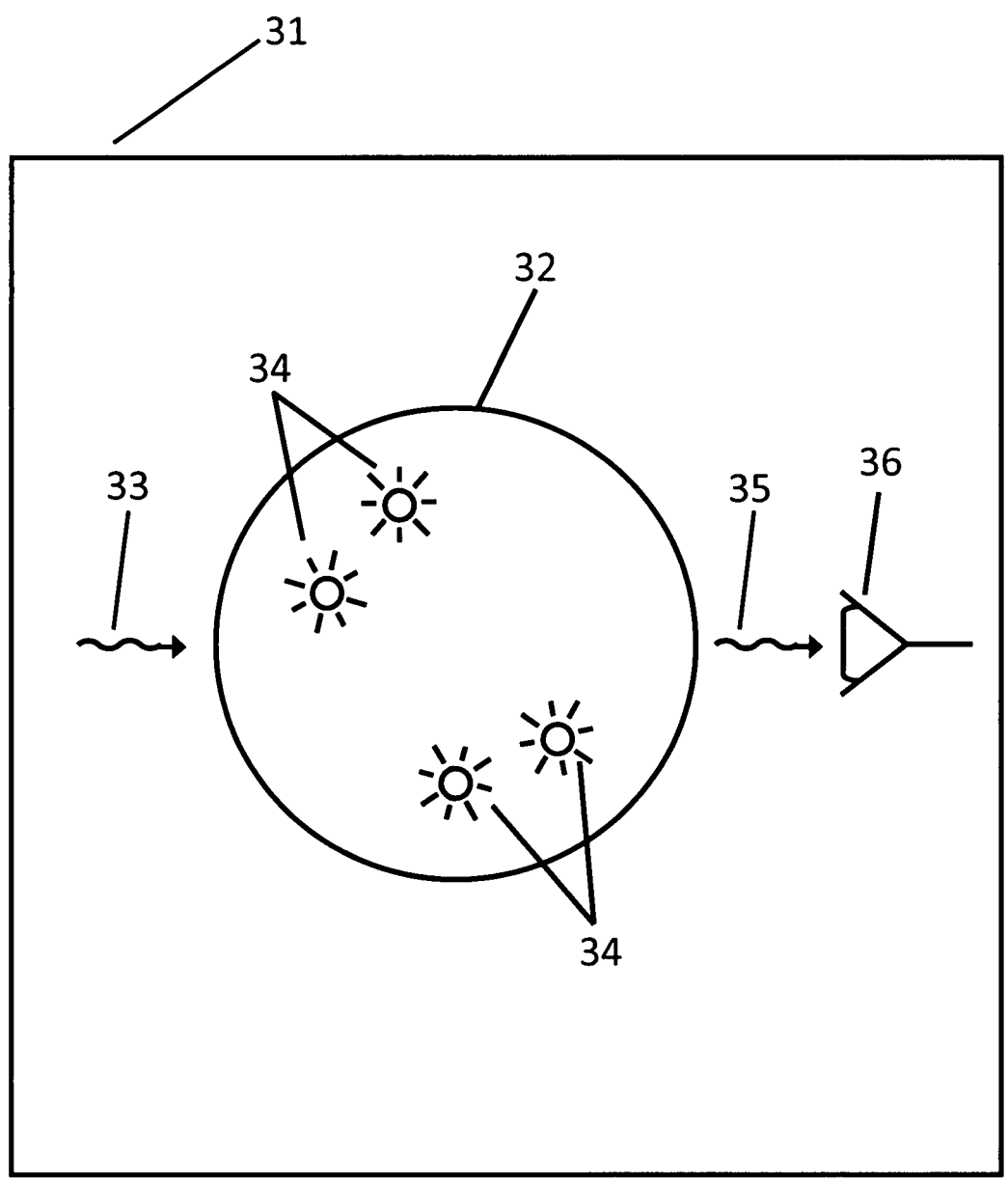
FIG. 11 shows an autofluorescence-based measurement of cell viability using the cytometric method and means of the invention.

For example, when the catheter of the present invention, e.g., neurocatheter, is used in either acute or chronic delivery conditions, the readings from said optical fibers (which serve as a sensor or as sensors) within the distal tip can provide a variety of useful physiological data that can play a central role in the optimization of the therapeutic approach. For instance, recordings of dopamine level can provide a quantitative indication of the functionality of the cells, thus implying that they either have or have not reached a certain stage of maturity in the differentiation process. Those data would then form the basis for clinical-strategy decisions on the need for delivery of growth factors, the timing of the delivery of said factors, and cessation of delivery of said factors FIG. 11 shows the catheter wall, 31, in which a port hole, 32, allows egress of the cell slurry containing autofluorescent cells, 34. Excitation light, 33, is incident on the cells, 34, as they pass through or near the region of the port hole, 32. The excitation light, 33, causes the cells, 34, to glow at a characteristic wavelength thus producing the optical emission, 35, which is observed by the detection system, 36. The media containing the cells can be of a density sufficiently high to insure full suspension of the cells. The media must be biocompatible with the target tissues into which the slurry will be infused. According to the method of the invention, the cells, 34, may have one characteristic autofluorescent emission when they are viable, and a different one when they are going through apoptosis.

Figure 12:
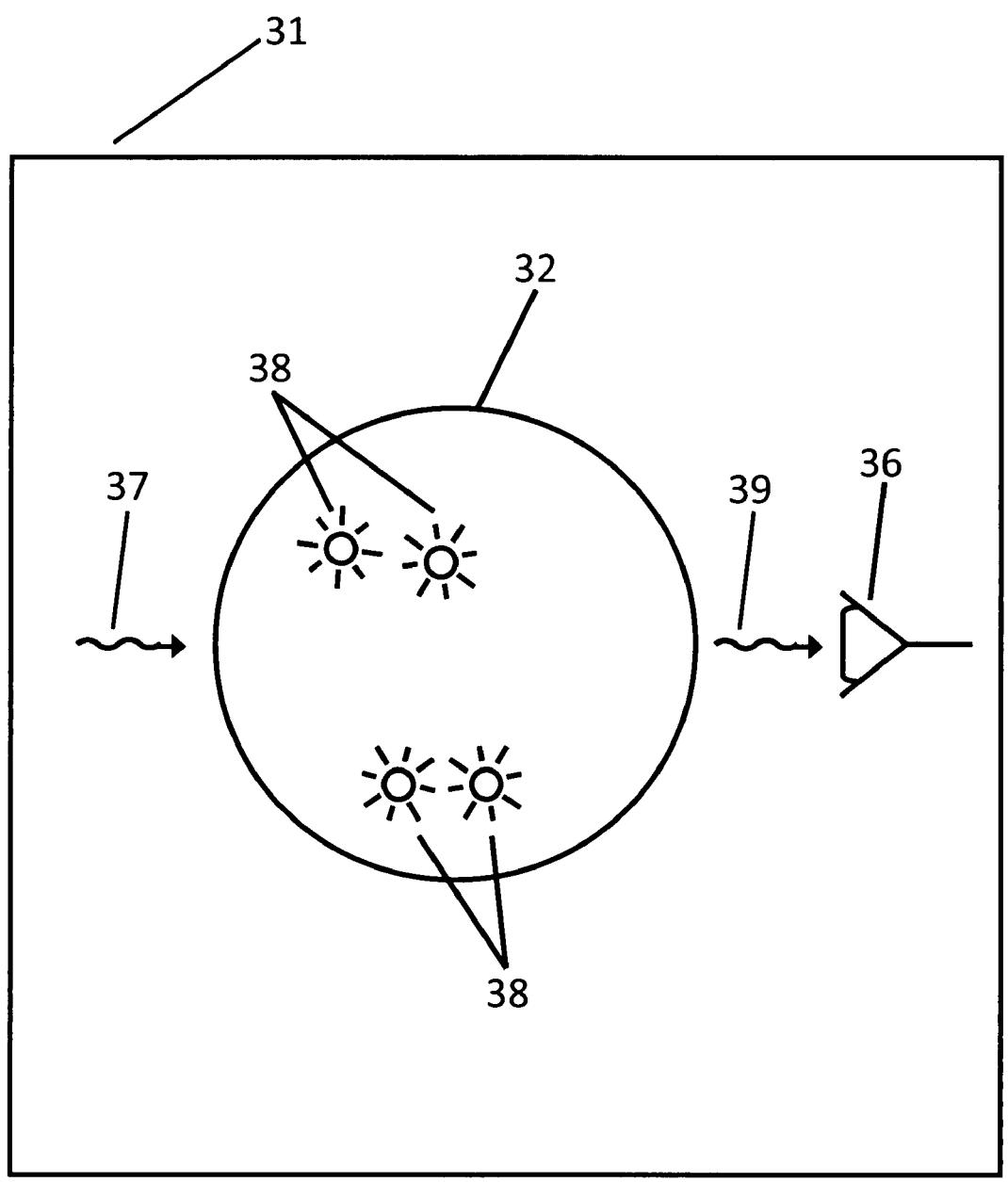
FIG. 12 shows vital stain-luminescence measurement of cell viability using the cytometric method and means of the invention.

FIG. 12 shows the catheter wall, 31, in which a port hole, 32, allows egress of the cell slurry containing vitally stained cells, 38. Interrogation light, 37, is incident on the cells, 38, as they pass through or near the region of the port hole, 32. The interrogation light, 37, interacts with the cells, 38, with the result that the luminescence, 39, associated with the interrogation is observed by the detection system, 36. As with the case of autofluorescent detection, the same considerations of media density and biocompatibility, and apoptotic signals will also apply.

Figure 13:
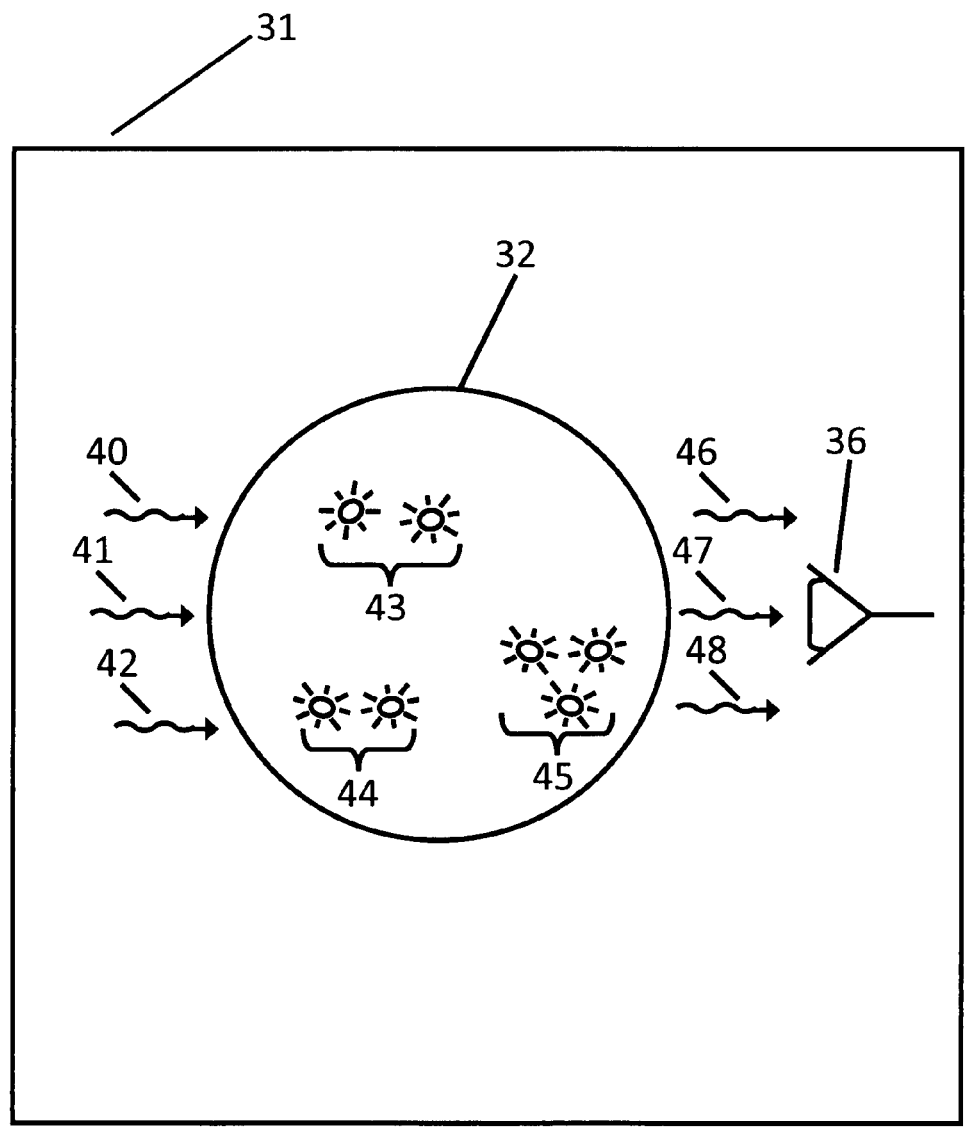
FIG. 13 shows a combined modality measurement of cell viability according to the multi-photon cytometric method and means of the invention.

FIG. 13 shows a multi-mode approach, in which excitation and interrogation beams, 40, 41, and 42, are incident on the region of the port hole, 32, located in the wall of the catheter, 1. Within this region are also located cell clusters, 43, 44, and 45, which have associated with them characteristic luminescent signals, 46, 47, and 49, arising in different cases from fluorescence, absorption and scattering. These signals are observed by detection system, 36. By employing a multi-mode photo-optical approach to the cytometric measurement of cell viability, it is possible to obtain independent measurements of the same variable (eg., number of viable cells), thus allowing confirmation of results, checking of measurement uncertainties, evaluation of systematic errors, and the like. In general several different types of optical sources can be used to create any of the excitation and interrogation beams that might be used in any of the embodiments of the invention. These include lasers, laser diodes, light emitting diodes, flash lamps, incandescent lamps, solid state emitters, and other such devices, systems, and means. Said optical sources may also be continuous wave or pulsed. When using pulsed sources, for example, pulsed laser light from short pulsed q-switched laser, said pulses might be used for the fluorescence detection process in such a way that it becomes possible to discriminate against scattering and media fluorescence, as might be done, for example, by fluorescence decay measurement or phase angle measurement. Also, according to the method and means of the invention, the invention may be practiced with autologous stem cells, NPCs, and those that have been differentiated either partially or fully into neurons.

Figure 14:
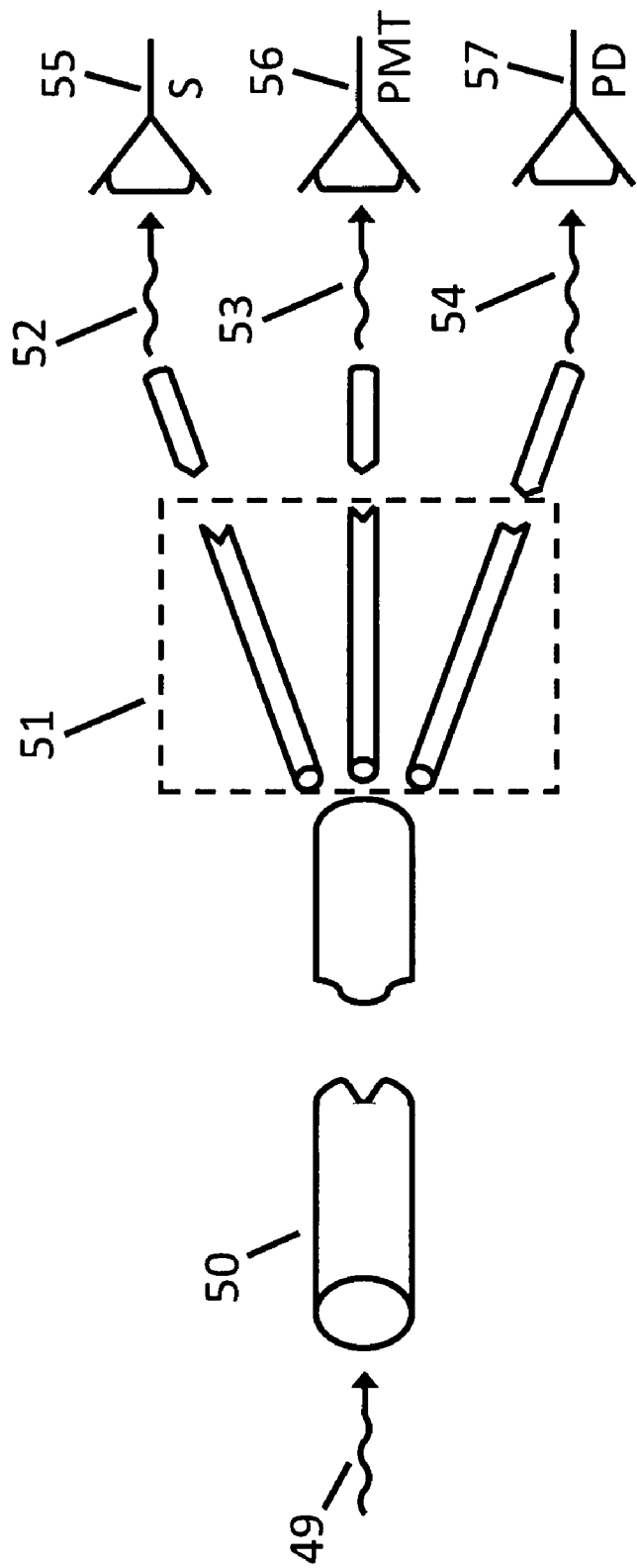
FIG. 14 shows a fiber-splitting means for employing any or all of the photo-optical cytometry means and methods of the invention.

FIG. 14 shows a photo-optical signal, 49, that has been emitted by the said cells, and the light of which is gathered into collection optical fiber, 50. A fiber beam splitter device, 51, is also shown schematically. The splitter, 51, is able to channel a plurality of individual photo-photo-optical signals, for example, 52, 53, and 54, into independent photo-detection means, such as spectrometer, 55, photomultiplier, 56, and photodiode, 57. Any of these detector means can incorporate band pass filters and laser light rejection filters. The optical fibers used in any of the embodiments of the invention might be of round, rectangular, or square cross-section, or of some other geometric cross-sectional structure. Homogenization of delivery beams and receiving fields of view via the physics of self-imaging can be accomplished by rectangular optics. Self-imaging in optical fibers is discussed by Allison and Gillies in, "Observations of and applications for self-imaging in optical fibers," Applied Optics, Vol. 33, No. 10, pps. 1801-1805, (1 Apr. 1994). Also in general, according to the method of the invention, when a spectrometer is used as the detection means, it is able to analyze the signal in such a way so as to discern between scattered laser light, media fluorescence and cell fluorescence. One or more data analysis algorithms might be employed on at least one digital computer for assessment of the results of the measurements and use of the results in control systems that are meant to regulate the number of viable cells being delivered through the catheter into the target tissues of the patient.

One skilled in the art can see that many other embodiments of inner lumen arrangements, sensor arrangements and numbers, and other details of construction and use constitute non-inventive variations of the novel and insightful conceptual means, system and technique which underlie the present invention.

While there has been shown and described what are at present considered the preferred embodiments of the invention, it will be obvious to those skilled in the art that various changes and modifications can be made therein without departing from the scope.

EXAMPLES

Example 1

An Example of a Catheter of the Present Invention

Figure 15:
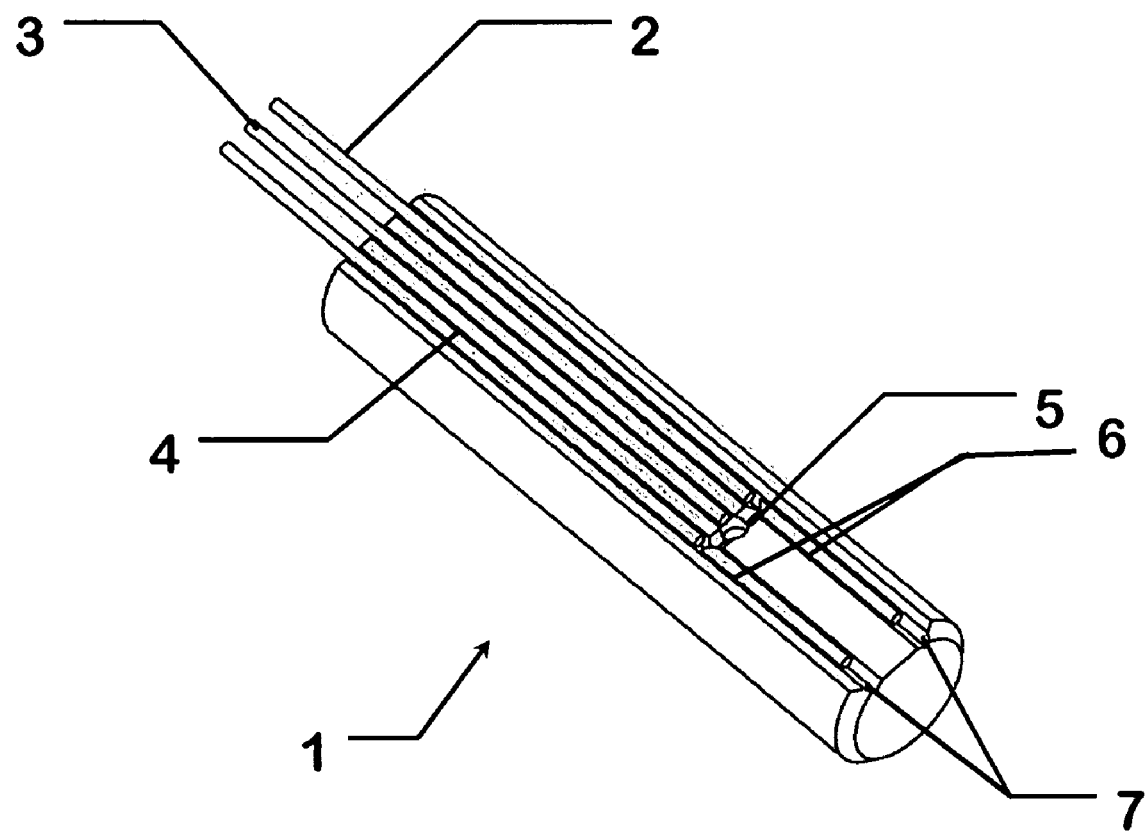
FIG. 15 shows a design of a modular tip with incorporated fiber optics for determination of the viability and quantity of delivered cells.

A modular tip compatible has been designed which incorporates optical fibers for the cytometric determination the number of viable cells exiting the port of the cell monitoring device. The catheter tip was machined from common brass, but for clinical prototypes, it might be made from a biocompatible material such as stainless steel, titanium or some MR-safe material. The CMD tip may be attached at the end of a catheter tube and contains a series of grooves for mounting the optical fibers as well as the catheter exit port. The fiber mounting grooves allow for the self-alignment of five optical fibers such that they are parallel to each other. Two fibers are polished at a 45° angle and coated with chrome such that they function as turning mirrors. The turning-mirror fibers require manual rotational and axial alignment. These fibers work together such that a beam of ultraviolet light for fluorescence excitation is delivered across the port hole of the catheter. The middle fiber serves to detect the excited fluorescence in the cells, and a second detection fiber serves to measure attenuation of the excitation beam within the cell slurry. The system uses the total fluorescent energy detected to determine the presence of cells and the density of cells in solution. FIG. 15 shows a schematic of the tip design.

Figure 16:
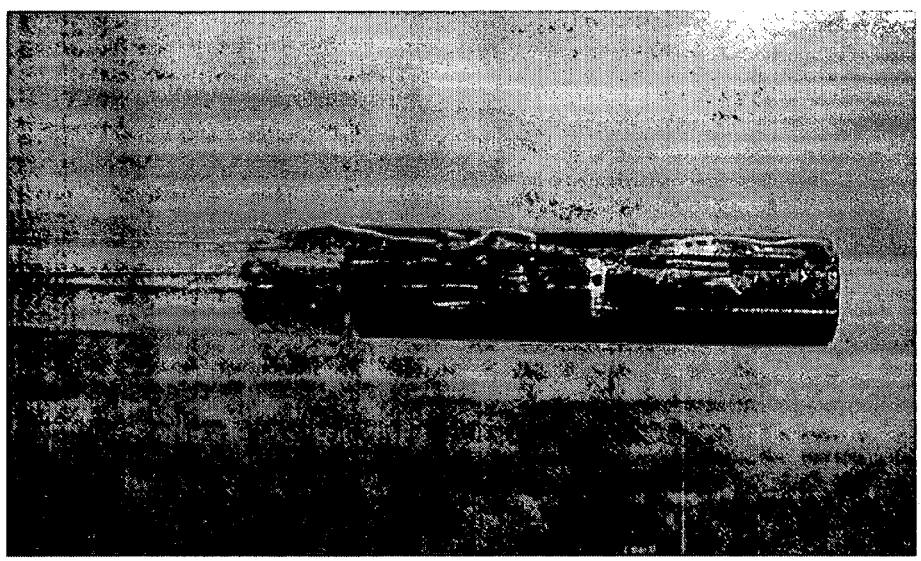
FIG. 16 shows a magnified view of prototype catheter tip showing laser illumination, and optical path.

The catheter tip has an outer diameter of 3.2 mm. The port hole is 0.38 mm in diameter and it contains three slots parallel to its axis for mounting the excitation and collection fibers and a transverse slot to allow the beam to cross the exit port hole. The two outer slots continue to the end of the tip to allow self-alignment of the turning mirror fibers axially with the excitation fiber and the outer collection fiber. Turning mirror fibers were fabricated by polishing fibers at a 45° angle, and evaporating a 1.0 μm layer of chromium on the fiber using an electron beam evaporation system. Fibers were spaced 0.25 mm apart and attached with ultraviolet light-curing epoxy. The total length of the tip is 12.5 mm. An enlarged view of the prototype tip is shown in FIG. 16.

Optical fibers were purchased from CeramOptec Industries (East Longmeadow, Mass.). The fibers used in the catheter experiments consisted of a 200 μm silica core. The fibers had 10 μm cladding of fluorine doped silica, and a 12.5 μm thick polyimide jacket for a total diameter of 245 μm. The numerical aperture (NA) of the fibers in these experiments was 0.37, having a half-angle of acceptance or illumination of 21.7°.

Fluorescence was excited using an Omnichrome (Chino, Calif.) Argon ion laser. Laser light was coupled into the fiber using a 10× microscope objective with an NA of 0.25. The argon ion laser is tunable over nine wavelengths including 454, 457, 465, 472, 476, 488, 496, 502, and 514 nm. The wavelength was selected to optimize the signal and to provide separation of the laser signal and the fluorescent excitation signal. Power output for these experiments is estimated to be approximately 10 mW based on maximum laser power output and power output setting. However estimate that coupling losses reduced the power significantly. An Ocean Optics (Dunedin, Fla.) USB2000 spectrometer which accepts fiber optic inputs was used to measure the output spectrum of the fluorescent signal.

Example 2

Fluorescence Measurements

Figure 17:
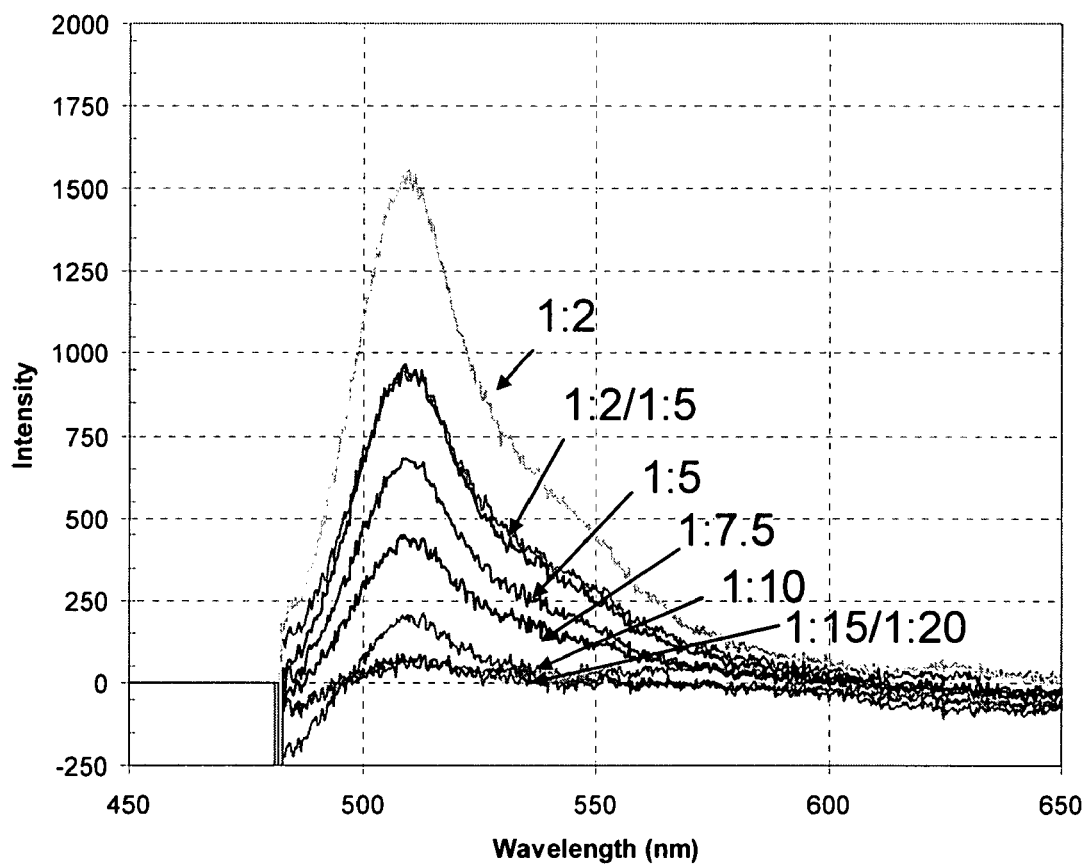
FIG. 17. Diluted aliquots from a $1.2 \times 10^6$ cells/mL suspension of GFP cells. Dilutions of this stock solution are placed in a stationary optical cell with the same optical configuration as the prototype catheter. Laser excitation is 458 nm.
Figure 18:
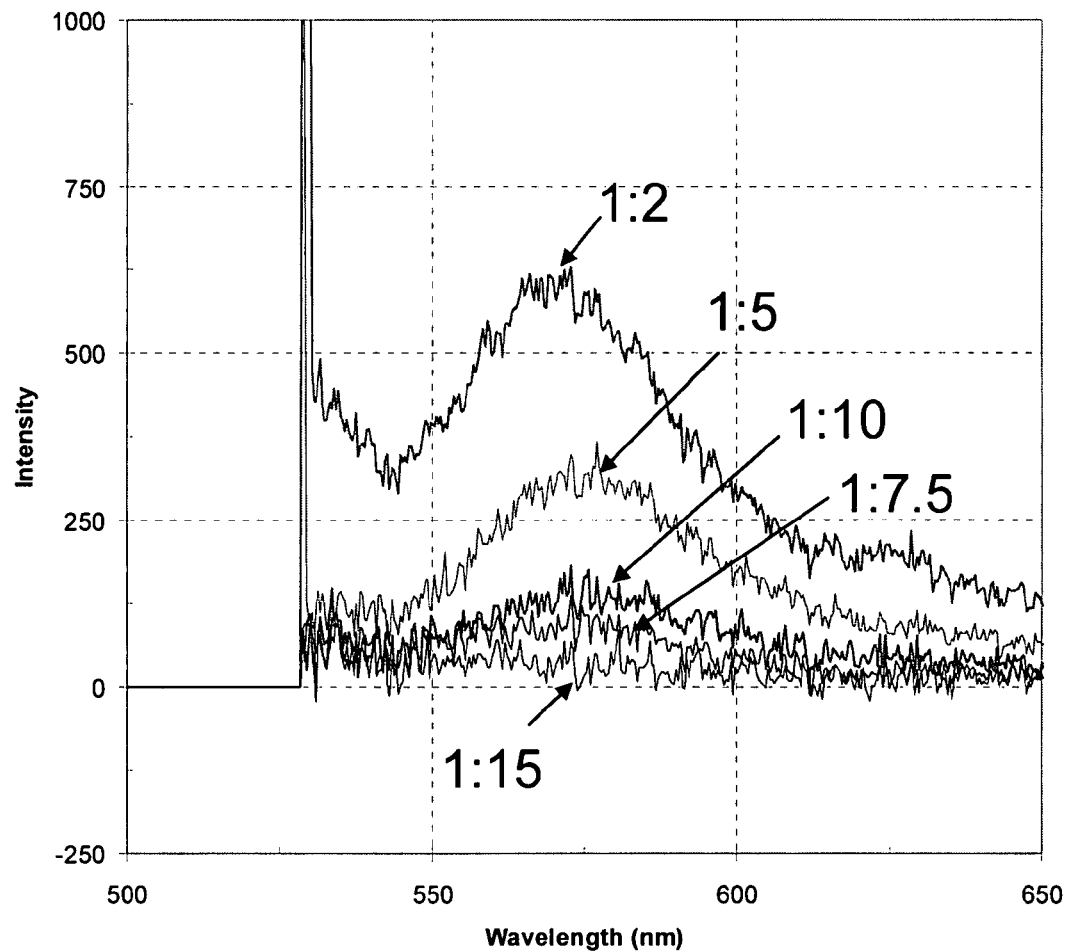
FIG. 18. Diluted aliquots from a $5.1 \times 10^5$ cells/mL suspension of RT2A cells stained using CellTracker™ Orange from Invitrogen. Laser excitation is 488 nm.

Petri dish experiments were performed with the fibers mounted in the configuration of FIGS. 15 and 16. Cell suspensions in aliquots of 0.25 mL were placed in the viewing field of this setup and fluorescence measurements were made. GFP transfected 3RT1 cells and non-transfected RT2A rat gliomal cells stained with CellTracker™ Orange (Invitrogen Corporation, Carlbad, Calif.) were used in these experiments. A stock solution of GFP cells at a density of $1.2 \times 10^6$ per milliliter and of RT2A cells at $5.1 \times 10^5$ per milliliter was used for this work. Cells were suspended in phosphate-buffered saline solution (PBS). Results of these experiments verify that the cell fluorescence can be detected using the fiber optic configuration, and that the total flourescence detected varies with cell density. Some variability in results was noted and is attributed to rapid settling of the cells in the medium. Laser excitation at 458 nm was used for GFP cells and at 488 nm for the stained RT2A cells. Results are shown in FIG. 17 and FIG. 18, respectively. The background signal for the PBS control sample was subtracted from the results for the cell suspensions.

Figure 19:
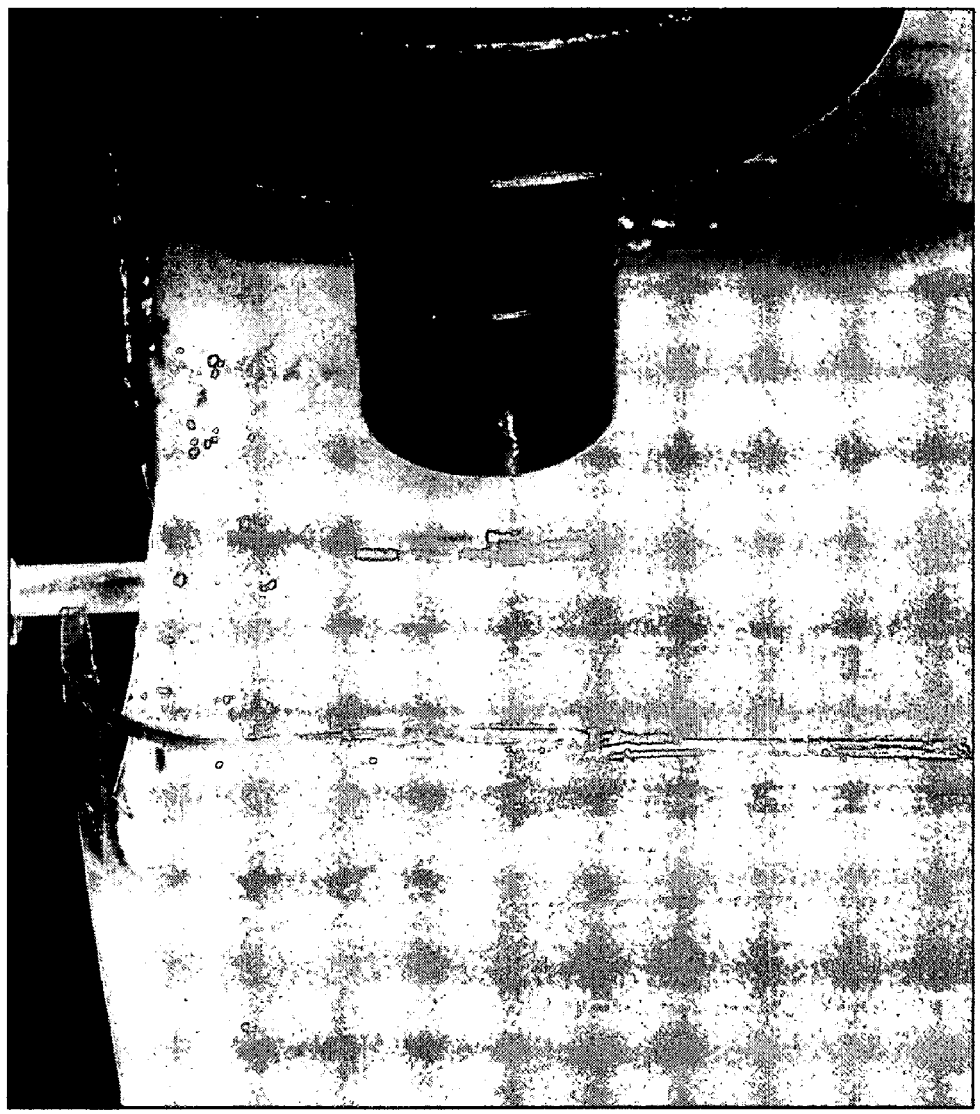
FIG. 19. The tip of the cell monitoring device is inserted within the brain phantom gel, and the objective of the videomicroscope looks down onto the experimental arrangement from above.
Figure 20:
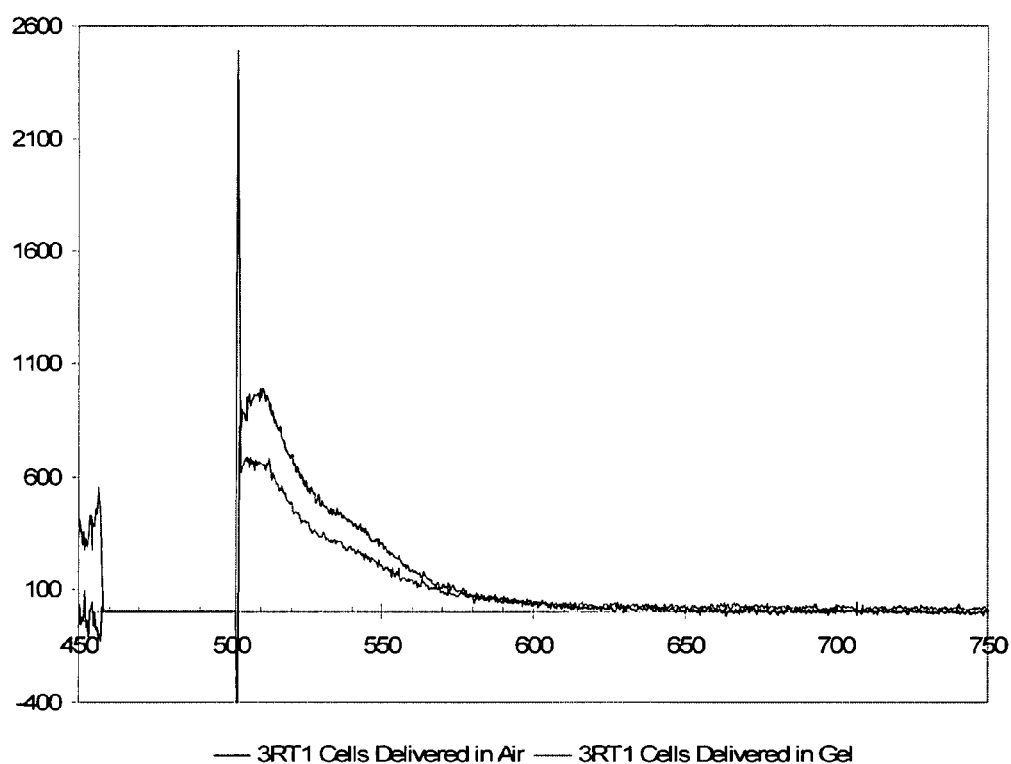
FIG. 20. Cells delivered in air and in a 0.6% agarose gel brain stimulant material. Cell density is $1.243 \times 10^6$ cells per milliliter. Flow rate is 100 microliters per minute. An excitation wavelength of 477 nm was used in this test of the neural cell delivery catheter. Background laser and PBS fluorescence signal has been subtracted.

Flow testing of the cell monitoring device has been performed both in air and using a 0.6% agarose gel that is often employed as a brain phantom material for in vitro infusion studies. Flow through the test apparatus was driven by a Bioanalytical Sciences (West Lafayette, Ind.) model MD 1000 syringe pump and a Hamilton (Reno, Nev.) model 81303 1.0 mL syringe. The flow rate for these experiments was 100 microliters per minute. A 3 mm flexible extension tube connected the syringe to the fiber optic-instrumented cell monitoring device. A video microscope was positioned above the exit port to observe the flow of the cell slurry as it emerged from the port. The overall experimental arrangement is shown in FIG. 19.

We claim:

1. A catheter comprising:
   a catheter body having an inner lumen, a distal end and a proximal end;
   a distal catheter tip body having a distal end and a proximal end, with the proximal end of said catheter tip body removably coupled to said catheter body distal end;
   at least one port hole in said catheter tip body at an intermediate distance between the distal and proximal ends of said catheter tip body;
   a plurality of alignment grooves axially aligned in said catheter tip body for the placement of optical fibers;
   at least one transverse groove connecting two or more axially aligned grooves adjacent to the exit point of at least one port hole;
   a mating mechanism for coupling said tip body to said catheter body;
   at least one internal structural chamber for passing material from said inner lumen to said at least one port hole;
   a plurality of optical fibers extending distally from the proximal end of said catheter tip body and ending adjacent to said at least one port hole, said plurality of optical fibers being disposed in said alignment grooves, wherein said plurality of optical fibers comprises at least one optical delivery fiber to deliver light adjacent to said at least one port hole, and wherein said plurality of optical fibers further comprises at least one optical collection fiber to collect light signals delivered across said at least one port hole;
   a plurality of optical fiber stubs disposed in said alignment grooves, comprising at least one first optical fiber stub extending proximally from the distal end of said catheter tip body and having a mirrored end facing the distal end of said at least one optical delivery fiber, and further comprising at least one second optical fiber stub extending proximally from the distal end of said catheter tip and having a mirrored end facing the distal end of said at least one optical collection fiber,
   wherein said at least one first optical fiber stub reflects light delivered by said at least one optical delivery fiber across said at least one port hole along said transverse groove, and wherein said at least one second optical fiber stub reflects the light reflected from said at least one first optical fiber stub towards said at least one optical collection fiber.

2. The catheter of claim 1 wherein said optical collection fibers collect fluorescence intensity, excitation, and scattering signals as cells pass through the said at least one port hole.

3. The catheter of claim 2 wherein the optical collection fibers collect fluorescence intensity, excitation and scattering signals at separate wavelengths.

4. The catheter of claim 1 wherein said mating mechanism further comprises at least one connecting device selected from the group consisting of tubular mechanical sleeve and bushing.

5. The catheter of claim 1 further comprising at least one micro-coil removably disposed on said distal catheter tip.

6. The catheter of claim 1 further comprising a magnetic resonance contrast enhancement agent.

7. The catheter of claim 1 further comprising radio-opaque materials.

8. The catheter of claim 1 further comprising multiple internal structural chambers.

9. The catheter of claim 1 wherein said optical fiber stubs further comprise concave mirrored surfaces.

10. The catheter of claim 1 wherein said optical fiber stubs can rotate to change the focal point of said reflected light.

11. The catheter of claim 1 further comprising a plurality of port holes.

12. A measurement and control system comprising a catheter according to claim 1, wherein the optical fibers in said catheter:
- deliver light across one or more port holes of said catheter;
- collect fluorescent signals emitted by cells or other materials or species being pumped through said one or more port holes;
- collect scattered light, scattered by cells or other materials or species being pumped through said one or more port holes;
- collect attenuated light that has been attenuated by cells or other materials or species being pumped through said one or more port holes; and
- convey said scattered and attenuated light along optical collection fibers to a measurement means that transduces the fluorescent or scattered light signals into electrical signals that are then converted to cytometric cell counts;
- whereby a pumping means is regulated in accordance with said cytometric cell counts to regulate the rates or amounts of slurry containing said cells or other materials or species delivered into said catheter.

13. The system of claim 12 wherein said optical fibers measure the levels of dopamine or other neurotransmitters, agents or chemicals in the interstitial space composing the neural niche for neurons and other cells within the brain of a patient.

14. The system of claim 12 wherein said system is operated manually by a clinician administering the treatment or is operated automatically by a computer-based or other automated data processing device, system, or means.

15. A method for in situ cytometric measurement of cell viability and count rates, the method comprising:
- inserting the catheter of claim 1 into a patient;
- delivering a cell slurry through a port hole of the catheter, wherein the cells in the slurry are autofluorescent or contain a fluorescent vital stain;
- exciting the cells with a wavelength of light to cause autofluorescence of the cells or fluorescence of the vital stain; and
- measuring autofluorescence or vital staining fluorescence of the cells, wherein the measurement of autofluorescence or vital stain fluorescence of the cell is a measurement of cell viability and count rates.

16. The method of claim 15, further comprising determining the number of cells in the cell slurry undergoing apoptosis.

17. The method of claim 15, wherein the catheter comprises fiber beam splitters for producing a plurality of individual channels of the light signal for subsequent readout by spectrometers, photomultiplier tubes, photodiodes and other such devices, systems and means.

18. The method of claim 15, in which an excitation and interrogation light is generated by one or more lasers, laser diodes, light emitting diodes, and other such devices, systems, and means.

19. The method of claim 15, wherein autofluorescence of the cells is measured.

20. The method of claim 15, wherein vital staining fluorescence is measured.

21. The method of claim 15, wherein both autofluorescence and vital staining fluorescence are measured.

* * * * *